United States Patent
Frommeyer et al.

(10) Patent No.: US 6,521,771 B2
(45) Date of Patent: Feb. 18, 2003

(54) USE OF ZINC TREATED WITH METAL HYDRIDE IN ORGANOMETALLIC SYNTHESIS

(75) Inventors: Georg Frommeyer, Erkrath (DE); Wilfried Knott, Essen (DE); Andreas Weier, Essen (DE); Jurij Weiss, Bochum (DE); Dagmar Windbiel, Essen (DE)

(73) Assignee: Goldschmidt AG, Essen (DE)

( * ) Notice: Subject to any disclaimer, the term of this patent is extended or adjusted under 35 U.S.C. 154(b) by 0 days.

(21) Appl. No.: 09/859,273

(22) Filed: May 17, 2001

(65) Prior Publication Data

US 2002/0014135 A1 Feb. 7, 2002

(30) Foreign Application Priority Data

May 19, 2000 (DE) .......................................... 100 24 776

(51) Int. Cl.$^7$ .............................. C07F 3/06; C07C 13/00
(52) U.S. Cl. ........................ 556/121; 556/128; 556/129; 585/20
(58) Field of Search ................................ 556/121, 128, 556/129

(56) References Cited

U.S. PATENT DOCUMENTS

| | | | |
|---|---|---|---|
| 2,989,557 A | | 6/1961 | Blitzer et al. ............ 260/429.9 |
| 3,050,541 A | | 8/1962 | Gould ......................... 260/448 |
| 3,077,490 A | | 2/1963 | Fernald ....................... 260/448 |
| 3,144,473 A | * | 8/1964 | Boor, Jr. et al. ............. 556/128 |
| 3,475,475 A | * | 10/1969 | Eidt .............................. 556/95 |
| 3,641,081 A | * | 2/1972 | Radtke ........................ 556/128 |
| 4,472,313 A | | 9/1984 | Giger et al. ................. 260/410 |
| 5,951,739 A | | 9/1999 | Klapdor et al. ............... 75/371 |
| 5,972,285 A | | 10/1999 | Knott ............................ 419/2 |

FOREIGN PATENT DOCUMENTS

| | | |
|---|---|---|
| BE | 559404 | 1/1958 |
| DE | 143 782 | 9/1980 |
| DE | 39 34 351 A1 | 4/1991 |
| DE | 41 01 630 C2 | 4/1992 |
| EP | 0 559 097 B1 | 5/1993 |
| EP | 1 031 634 A1 | 8/2000 |
| GB | 2 268 489 A * | 12/1994 |
| JP | 5-287361 | 11/1993 |

OTHER PUBLICATIONS

Han, et al., "Organic Sonochemistry. Sonic Acceleration of the Reformatsky Reaction," J. Org. Chem. 1982, 5030–5032.

Von Alois Fürstner, "Chemie von und mit hochaktiven Metallen," Angew. Chem, 1993, 105, 171–197.

Takai, et al, "A Dramatic Effect of a Catalytic Amount of Lead on the Simmons–Smith Reaction and Formation of Alkylzinc Compounds from Iodoalkanes. Reactivity of Zinc Metal: Activation and Deactivation," J. Org. Chem. 1994, 59, 2671–2673.

Rawson, et al., "A Convenient Procedure for the Methylenation of Olefins to Cyclopropanes," J. Org. Chem., vol. 35, No. 6, 1970, 2057–2058.

Sakamoto, et al., "Thermodynamic Properties for Solution of Hydrogen in Palladium–Based Binary Alloys," Ber. Bunsenges. Phys. Chem. 99, 807–820 (1995) No. 6.

Shank, et al, "Simplified Zinc–Copper Couple for Use in Preparing Cyclopropanes from Methylene Iodide and Olefins," J. Org. Chem, 1959, 24, 1825–1826.

LeGoff, "Cyclopropanes from an Easily Prepared, Highly Active Zinc–Copper Couple, Dibromomethane, and Olefins," J. Org. Chem, 1964, 29, 2048–2050.

Simmons and Smith, "A New Synthesis of Cyclopropanes From Olefins," J. Am. Chem. Soc., 1958, 80, 5323–5324.

Simmons and Smith, "A New Synthesis of Cyclopropanes," J. Am. Chem. Soc., 1959, 81, 4256–4264.

Houben–Weyl, "Methoden zur Herstellung organischer Aluminium–Verbindungen," Methoden der organischen Chemie, 1970, vol. 13/4, 33.

Houben–Weyl, "Unwandlung von Organo–zink–Verbindungen durch Reaktion mit Olefinen, Acetylenen, Silanen und Stannanen," Methoden der organischen Chemie, 1973, vol. 13/2a, 838–852.

Houben–Weyl, "Reformatsky–Synthese," Methoden der organischen Chemie, 1973, vol. 13/21, 809–838.

Rieke, et al., "Activated Metal. XI. An Improved Procedure for the Preparation of β–Hydroxy Esters Using Activated Zinc," Synthesis, 1975, 452–453.

Bönnemann, et al., "Herstellung feinverteilter Metall– und Legierungspulver," Angew. Chem., 1990, 102, 324–326.

* cited by examiner

*Primary Examiner*—Porfirio Nazario-Gonzalez
(74) *Attorney, Agent, or Firm*—Frommer Lawrence & Haug LLP

(57) ABSTRACT

The present invention describes the use of zinc treated with metal hydride in organometallic synthesis.

8 Claims, No Drawings

USE OF ZINC TREATED WITH METAL HYDRIDE IN ORGANOMETALLIC SYNTHESIS

RELATED APPLICATIONS

This application claims priority under 35 USC §119 to German application 100 24 776.8, filed May 19, 2000, herein incorporated by reference.

BACKGROUND OF THE INVENTION

1. Field of the Invention

The present invention describes the use of zinc treated with metal hydride in organometallic synthesis.

2. Background of the Invention

The still unpublished European application 00102815.8 discloses the reaction of metallic zinc with metal hydrides, in particular magnesium hydride. The relevant contents of this patent application are hereby fully incorporated by reference.

Previous fields of application of hydrides in metallurgy or materials science are restricted mainly to use for producing metal foams (for example $TiH_2$ or $MgH_2$ as blowing agent for aluminum foams; U.S. Pat. No. 5,972,285; DE-C41 01 630; EP-B-0 559 097), production of microcrystalline or amorphous metals or alloys by reduction of corresponding metal salts by means of hydrides (U.S. Pat. No. 5,951,739; DE-C-3 934351; Bönnemann, Brijoux, Joussen, Angew. Chem., 1990, 102, 324–326), solid-state phase transformations of alloys via hydride formation by treatment with hydrogen (Sakamoto, Chen, Ura, Flanagan, Ber. Bunsen-Ges. 1995, 99, 807–820), decarburization of steel by means of hydrides (JP-C-05 287 361) and the activation of aluminum by means of alkali metal hydrides or alkaline earth metal hydrides for the synthesis of aluminum alkyls (Houben-Weyl, Methoden der organischen Chemie, 1970, volume 13/4, 33; U.S. Pat. No. 2,989,557; U.S. Pat. No. 3,050,541; BE-C-559 404; U.S. Pat. No. 3,077,490).

In the field of organic chemistry, organometallic zinc reagents open up important routes to a series of pharmaceuticals (for example steroids), derivatives of natural products (for example terpenes, fatty acids) and insecticides (for example pyrethroids).

As representative examples of the use of zinc in organometallic reactions, its use in Simmons-Smith and Reformatsky reactions will be described here.

In Simmons-Smith reactions, olefins are reacted with diiodomethane and metallic zinc, typically in diethyl ether as solvent, to form cyclopropanes. According to the literature (Houben-Weyl, Methoden der organischen Chemie, 1973, volume 13/2a, 838–852, herein incorporated by reference), $CH_2I_2$ and Zn first form the insertion product $ICH_2ZnI$, as reactive intermediate, and this subsequently transfers carbene $CH_2$ to the double bond of the olefin used with elimination of $ZnI_2$ in a single-stage mechanism.

In Reformatsky reactions, α-halo esters are reacted with metallic zinc and aldehydes or ketones to give β-hydroxycarboxylic esters. In the first step, according to the literature (Houben-Weyl, Methoden der organischen Chemie, 1973, volume 13/2a, 809–838, herein incorporated by reference), the zinc inserts into the halogen-carbon bond of the α-halo ester to form a nucleophilic organozinc intermediate which in the second step reacts with the electrophilic carbonyl carbons of aldehydes or ketones to give β-hydroxycarboxylic esters.

In the two types of reaction described, a very high product yield requires not only suitable reaction conditions (type of solvent, temperature, choice of concentrations, reaction time, etc.) but also appropriate pretreatment or activation of the metallic zinc used. To increase the reactivity (destruction of the oxide layer, achievement of a particularly fine division) of zinc in Simmons-Smith and Reformatsky reactions, numerous physical methods (for example mechanical milling, use of ultrasound, metal vaporization, electrolytic ultra-high purification) and chemical methods (for example Rieke processes, zinc-copper couple formation, etching processes, potassium-graphite processes) have been developed in the past (A. Fürstner, Active Metals, Preparation, Characterization, Applications, VCH, 1996).

As a criterion for the quality or efficiency of the physical or chemical activation method employed in each case, the use of the respective treated metallic zinc can be tested in organometallic synthetic chemistry, for example in Simmons-Smith and Reformatsky reactions, by determining the product yield in each case.

Simmons and Smith (J. Am. Chem. Soc., 1958, 80, 5323–5324; J. Am. Chem. Soc., 1959, 81, 4256–4264) themselves describe what they call the cyclopropanation reaction using a zinc-copper couple which was obtained in a relatively complicated fashion by reduction of a copper oxide/zinc mixture in a stream of hydrogen at 500° C. Later work by other authors repeatedly emphasizes the problems of a good and reproducible method of preparing the zinc-copper couple and propose alternative methods (for example Shank, Shechter, J. Org. Chem, 1959, 24, 1825–1826; LeGoff, J. Org. Chem., 1964, 29, 2048–2050). The simplest method of preparation may well be that descried by Rawson and Harrison (J. Org. Chem., 1970, 35,2057–2058).

They produce the zinc-copper couple by heating a suspension of zinc containing 10% of copper(I) chloride for 30 minutes. More recent work on alternatives to the zinc-copper couple include, for example, the use of electrolytically ultra-highly purified zinc (Takai, Kakiuchi, Utimoto, J. Org. Chem., 1994, 59, 2671–2673), the use of zinc activated by means of small amounts of elemental iodine in steroid synthesis (DD-C-143 782) or the use of catalytic amounts of hydride complexes such as sodium bis(2-methoxyethoxy) aluminum hydride (Vitride®) in the cyclopropanation of unsaturated fatty acid esters (U.S. Pat. No. 4,472,313).

For use of zinc in Reformatsky reactions, a similar type and variety of activation methods as described above for Simmons-Smith reactions is employed. Simple activation by means of reagents such as iodine, dibromomethane, etc., or washing with dilute mineral acids frequently gives only moderate success. Once again, the use of specific alloys (for example zinc-copper or zinc-silver couples) is substantially more effective. A very effective chemical activation method is the reduction of zinc halides by potassium in the Rieke process. Further methods include reduction using potassium-graphite or the use of ultrasound (Fürstner, Angew. Chem., 1993, 105, 171–197; Rieke, Uhm, Synthesis, 1975, 452–453; Han, Boudjouk, J. Org. Chem., 1982, 47,5030–5032).

All the abovementioned activation methods for zinc have the disadvantage that they are either relatively complicated and costly or have only very restricted applicability or effectiveness, or lead to unreproducible yields. The industrial problem of an efficient and economical way of carrying out further organozinc reactions which are not encumbered by the abovementioned disadvantages has thus not been solved hitherto.

It has surprisingly been found that treatment of molten zinc with metal hydrides produces zinc which overcomes the abovementioned disadvantages extremely well and can be employed directly and efficiently in organometallic syntheses without using the above-described activation methods of the prior art.

SUMMARY OF THE INVENTION

According to the invention, it has been found that commercially available metallic zinc which is heated together with about 2% by weight of metal hydride (for example LiH, $MgH_2$, $AlH_3$, $TiH_2$, etc.) or metal hydride mixtures to the melting point and then cooled to room temperature and converted mechanically into turnings leads to significantly higher product yields in Simmons-Smith and Reformatsky reactions both with (by means of zinc-copper couple formation in the case of Simmons-Smith reactions) and without the abovementioned additional activation methods than does commercially available zinc powder.

As an alternative, the treatment of zinc according to the invention can also be carried out in a molten phase by bringing the zinc melt into contact with metal hydride or metal hydride mixtures. Accordingly, measures which serve to rapidly disperse the metal hydride(s) in the liquid zinc matrix (stirring, blowing inert gases into the melt, etc.) are advantageously used in this variant of the process of the invention.

DETAILED DESCRIPTION OF THE INVENTION

When the zinc obtained by the above-described treatment process was used in Simmons-Smith reactions carried out by the literature method (R. J. Rawson, I. T. Hanison, J. Org. Chem. 1970, 35, 2057–2058, herein incorporated by reference), new and surprising results were able to be obtained.

A test reaction chosen was, for example, the conversion of cyclohexene into norcarane using $CH_2I_2$ as carbene transferer.

The yields of norcarane when using zinc which has been treated with metal hydride and activated with 10% of copper(I) chloride were 5% higher than when using commercial zinc which had likewise been activated with 10% of copper(I) chloride.

As test reaction for comparative reactivity studies in Reformatsky reactions to compare zinc which has been obtained by pretreatment with hydrides and commercially available zinc, the yields in the synthesis of ethyl 3-hydroxybutyrate from ethyl bromoacetate/acetaldehyde and the yields in the synthesis of ethyl 3-hydroxyoctanoate from ethyl bromoacetate/hexanal were determined (Houben-Weyl, Methoden der organischen Chemie, 1973, volume 13/2a, 818). Both batches of zinc are used without any further customary activation.

In the synthesis of ethyl 3-hydroxybutyrate, it has been found that the product yield when using zinc treated with metal hydride is 7% higher than when using the commercial batch of zinc.

A similar trend is found in the synthesis of ethyl 3-hydroxyoctanoate. The product yield was able to be increased by an average of 4% when using hydride-pretreated zinc compared to commercial zinc.

In all investigations according to the present invention on the use of zinc treated with metal hydride in the synthesis of organozinc reagents, it could clearly be seen that significantly higher product yields than when using commercial batches of zinc can be achieved. This is all the more astonishing when one remembers that the reactivity studies presented were carried out using turnings of zinc treated with metal hydride which had a significantly lower available metal surface area in contrast to commercially available zinc powder. Furthermore, the generally accepted view that only the use of a zinc-copper couple in Simmons-Smith reactions leads to high yields of cyclopropanation products was surprisingly able to be clearly disproved. The investigations carried out surprisingly present exactly the opposite picture. Dispensing with the "activated metal couple" even leads to an increased reactivity when zinc treated with metal hydride is used, as the results impressively demonstrate.

It could very clearly be seen that the significantly higher activity of the zinc treated with metal hydride compared to commercial zinc in organometallic synthetic chemistry has a decisive positive effect on the product yield. It is obvious that a similarly distinct positive effect on further important and decisive reaction parameters such as reaction time, reaction temperature, stereoselectivity and regioselectivity, etc., can be achieved.

Viewed purely formally, the Simmons-Smith reaction is, according to the literature (Houben-Weyl, Methoden der organischen Chemie, 1973, volume 13/2a, 838–852, herein incorporated by reference), is an addition reaction involving the organozinc compound $CH_2X_2ZnX$ which is formed as an intermediate from Zn and $CH_2X_2$ (X=Br, I) and can also be isolated and which reacts with an olefin to form a cyclopropane with elimination of $ZnX_2$. Accordingly, there are further possible uses of the zinc according to the present invention in the synthesis and isolation of organozinc compounds such as dialkylzinc, diarylzinc, alkylarylzinc, alkylzinc halide, arylzinc halide, zinc dihydride, alkylzinc hydride, arylzinc hydride, dialkylzinc alkoxide, diarylzinc alkoxide, alkylzinc alkylalkoxide, alkylzinc arylalkoxide, arylzinc alkylalkoxide, arylzinc arylalkoxide, zinc dialkylamide, zinc diarylamide, alkylzinc alkylamide, alkylzinc arylamide, arylzinc alkylamide and arylzinc arylamide compounds.

The invention will now be illustrated by the following examples, without a restriction of its scope being implied. The experiments described below were carried out in an argon atmosphere. Air- and water-free solvents were used. Toluene and diethyl ether were dried over sodium. The organic and inorganic starting materials used were employed without further purification or drying.

The following were used: dibromomethane (99%), methyl trans-crotonate (98%), ethyl bromoacetate (98%), acetaldehyde (99.5%) and hexanal (96%) from Acros; cyclohexene (99%) and 4-vinylcyclohexene (99%) from Aldrich; Diiodomethane, copper(I) chloride (96%) and zinc powder for the reactivity studies from Fisher Scientific (97.2%). For the treatment of zinc with hydrides, use was made of zinc powder from Grillo-Werke AG (99.95%).

EXAMPLES

Reference Example 1
Process for Treating Metallic Zinc with Magnesium Hydride 294 g of commercial zinc powder were mixed intensively with 6 g of magnesium hydride powder (Tego® Magnan) for 10 minutes, then pressed in a steel capsule under a pressure of 200 metric tons and subsequently heated at 450° C. under argon in an open induction furnace for 10 minutes. After cooling to room temperature, the solid zinc block obtained was machined without using lubricants or coolants to produce turnings having an average size of 2×10 mm.

Example 1
Preparation of Norcarane using Zinc Pretreated as Described in Reference Example 1 and Activation by Means of Copper (I) chloride 8.5 g (0.13 mol) of zinc and 1.29 g (0.013 mol) of copper(I) chloride were suspended in 40 ml of diethyl ether and the mixture was refluxed while stirring for 30 minutes. 5.25 ml (0.065 mol) of diiodomethane and 5.05 ml (0.05 mol) of cyclohexene were subsequently added and the mixture was refluxed while stirring for another 24 hours. The mixture was filtered and the organic phase was extracted twice with 20 ml of 5% strength hydrochloric acid and three times with 20 ml of water. The combined aqueous phases were extracted again with 30 ml of diethyl ether. The combined organic phases were dried over $Na_2SO_4$. Yield of norcarane (GC analysis): 71%.

Example 2

Preparation of Norcarane 8.5 g (0.13 mol) of zinc pretreated as described in Reference Example 1 without activation, 5.25 ml (0.065 mol) of diodomethane and 5.05 ml (0.05 mol) of cyclohexene were suspended in 40 ml of diethyl ether and the mixture was refluxed while stirring for 24 hours. The mixture was filtered and the organic phase was extracted twice with 20 ml of 5% strength hydrochloric acid and three times with 20 ml of water. The combined aqueous phases were extracted again with 30 ml of diethyl ether. The combined organic phases were dried over $Na_2SO_4$. Yield of norcarane (GC analysis): 82%.

Comparative Example 1

Example 1 was Repeated Using Commercial Zinc. The yield was 66%.

Even more amazing was the observation that the yield of norcarane could be increased by 16% when using the zinc treated with metal hydride compared to commercial zinc activated with 10% of copper(I) chloride when activation with copper was omitted. Table 1 below summarizes the data for the reaction.

TABLE 1

| | $Zn/CH_2I_2$/Cyclohexene ratio [mol] | CuCl [mol] | $Et_2O$ [ml] | Yield [GC-%] |
|---|---|---|---|---|
| Example 1 | 0.13/0.065/0.05 | 0.013 | 40 | 71 |
| Comp. Ex. 1 | 0.13/0.065/0.05 | 0.013 | 40 | 66 |
| Example 2 | 0.13/0.065/0.05 | — | 40 | 82 |

Example 3

4% higher yields of norcarane could be achieved in the reaction of cyclohexene with $CH_2Br_2$ as carbene source when using the zinc treated with metal hydride compared to commercial zinc when both batches of zinc were activated with 10% of copper(I) chloride.

TABLE 2

| | $Zn/CH_2Br_2$/Cyclohexene ratio [mol] | CuCl [mol] | $Et_2O$ [ml] | Yield [GC-%] |
|---|---|---|---|---|
| Example 3 | 0.065/0.0325/0.025 | 0.0065 | 20 | 77 |
| Comp. Ex. 2 | 0.065/0.0325/0.025 | 0.0065 | 20 | 73 |

Examples 4, 5, Comparative Example 3

Further to the above examples, it was found, using the procedures of Examples 1 and 2, that the reaction of 4-vinylcyclohexene with zinc treated with metal hydride gave 71% of cyclopropanation products when activation with 10% of copper(I) chloride is employed and gave a product yield of 72% without activation using 10% of copper(I) chloride. The analogous reaction using commercial zinc and copper activation gave a yield of only 40%.

Table 3 below summarizes the reaction data.

TABLE 3

| | $Zn/CH_2I_2$/4-Vinylcyclohexene ratio [mol] | CuCl [mol] | Total Yield [GC-%] |
|---|---|---|---|
| Example 4 | 0.065/0.0325/0.025 | 0.0065 | 71 |
| Comp. Ex. 3 | 0.065/0.0325/0.025 | 0.0065 | 40 |
| Example 5 | 0.065/0.0325/0.025 | — | 72 |

Example 6, Comparative Example 4

A further aspect was that the product yield obtained by the procedures of Examples 1 and 2 in the cyclopropanation of methyl trans-crotonate when using zinc which had been treated by the above-described process and had not been activated with 10% of copper(I) chloride could be increased by 21% compared to commercial zinc with appropriate activation using copper(I) chloride.

The table below summarizes the reaction data obtained.

TABLE 4

| | $Zn/CH_2I_2$/methyl trans-crotonate ratio [mol] | CuCl [mol] | $Et_2O$ [ml] | Yield [GC-%] |
|---|---|---|---|---|
| Comp. Ex. 4 | 0.13/0.065/0.05 | 0.013 | 20 | 16 |
| Example 6 | 0.13/0.065/0.05 | — | 20 | 37 |

Example 7, Comparative Example 5

Preparation of Ethyl 3-hydroxybutyrate 15.28 g (0.234 mol) of zinc pretreated as described in Reference Example 1 were suspended in 50 ml of toluene, the mixture was heated to 83° C., the heat source was subsequently removed and a mixture of 22.8 ml (0.206 mol) of ethyl bromoacetate and 10.45 ml (0.187 mol) of acetaldehyde was added dropwise over a period of 30 minutes. After a brief induction phase, rigorous foaming and heating of the reaction mixture to 110° C. was observed. After all the mixture had been added, the resulting suspension was cooled to 10° C. by means of an ice/water mixture, after which 30 ml of 50% strength sulfuric acid was added dropwise at such a rate that the temperature of the suspension did not exceed 35° C. After phase separation, the organic phase was washed once with 30 ml of 5% strength sodium carbonate solution and the combined aqueous phases were extracted twice with 30 ml of carbon tetrachloride. The combined organic phases were dried over sodium sulfate. After filtration and removal of all volatile constituents on a rotary evaporator at 40° C./5 torr, the residue obtained was distilled in an oil pump vacuum at 3.5 torr. The fraction comprising ethyl 3-hydroxybutyrate goes over at 58–60° C. Yield: 7.5 ml (31%).

When the procedure of Example 7 was repeated using commercial zinc powder, a product yield of 24% was achieved.

TABLE 5

| | Zn/ethyl bromoacetate/hexanal ratio [mol] | Yields [%] |
|---|---|---|
| Example 7 | 0.117/0.103/0.0935 | 59, 65, 70 |
| Comp. Ex. 5 | 0.117/0.103/0.0935 | 69, 61, 54 |

Example 8

Preparation of Ethyl 3-hydroxyoctanoate 7.64 g (0.117 mol) of zinc pretreated as described in Reference Example 1 were suspended in 50 ml of toluene, the mixture was heated to 83° C., the heat source was subsequently removed and a mixture of 11.4 ml (0.103 mol) of ethyl bromoacetate and 11.23 ml (0.0935 mol) of hexanal was added dropwise over a period of 30 minutes. After a brief induction phase, rigorous foaming and heating of the reaction mixture to 110° C. was observed. After all the mixture had been added, the resulting suspension was cooled to 8° C. by means of an ice/water mixture, after which 15 ml of 50% strength sulfuric acid was added dropwise at such a rate that the temperature of the suspension did not exceed 35° C. After phase separation, the organic phase was washed twice with 15 ml of water and dried over sodium sulfate. After filtration and removal of all volatile constituents on a rotary evaporator at 50° C./5 torr, the residue obtained was distilled in an oil pump vacuum at 2.5 torr. The fraction comprising ethyl 3-hydroxyoctanoate went over at 88–93° C. Yield: 12.25 g (70%).

The above description is intended to be illustrative and not limiting. Various changes and modification in the embodiment described herein may occur to those skilled in the art. Those changes can be made without departing from the scope and spirit of the invention.

What is claimed is:

1. In a process for the preparation of organozinc compounds by organo compounds with metallic zinc, the improvement which comprises using metallic zinc, which has been contacted in liquid form or as a zinc melt with one or more metal hydrides and cooling the liquid or melt to room temperature.

2. The process according to claim 1, wherein the metal hydride is LiH, $MgH_2$, $AlH_3$ or $TiH_2$ or a mixture of these metals.

3. The process according to claim 1, wherein the metal hydride is $MgH_2$.

4. The process according to claim 1, wherein the contacted metallic zinc contains about 2% by weight of metal hydride.

5. The process according to claim 1, wherein the contacted metallic zinc is in the form of a powder.

6. The process according to claim 1, wherein the contacted metallic zinc is in the form of turings.

7. The process according to claim 1, wherein the organozinc compound is in an organozinc intermediate.

8. The process according to claim 1, wherein the organozinc compound is dialkylzinc, diarylzinc, alkylarylzinc, alkylzinc halide, arylzinc halide, zinc dihydride, alkylzinc hydride, arylzinc hydride, dialkylzinc alkoxide, diarylzinc alkoxide, alkylzinc alkylalkoxide, alkylzinc arylalkoxide, arylzinc alkylalkoxide, arylzinc arylalkoxide, zinc dialkylamide, zinc diarylamide, alkylzinc alkylamide, alkylzinc arylamide, arylzinc alkylamide or arylzinc arylamide compounds.

* * * * *